United States Patent [19]
Zadini et al.

[11] Patent Number: 5,520,650
[45] Date of Patent: May 28, 1996

[54] SELF-ARRESTING OVERPENETRATION-PROOF CANNULA DEVICE FOR BODY CAVITIES

[76] Inventors: Filiberto Zadini, 16814 Rayen St., North Hills, Calif. 91343; Giorgio Zadini, 2237 Hilltop La., Camarillo, Calif. 93012

[21] Appl. No.: 296,492

[22] Filed: Aug. 25, 1994

[51] Int. Cl.$^6$ ................................................ A61M 5/00
[52] U.S. Cl. ............................................ 604/117; 604/263
[58] Field of Search .................................. 604/117, 192, 604/198, 263, 165

[56] References Cited

U.S. PATENT DOCUMENTS

| | | | |
|---|---|---|---|
| 2,047,010 | 7/1936 | Dickinson | 604/117 |
| 3,530,785 | 9/1970 | Peters et al. | 604/117 |
| 4,269,192 | 5/1981 | Matsuo | 604/117 |

FOREIGN PATENT DOCUMENTS

| | | | |
|---|---|---|---|
| 1022758 | 1/1958 | Germany | 604/117 |
| 133559 | 1/1960 | U.S.S.R. | 604/117 |
| 2071499 | 9/1981 | United Kingdom | 604/117 |

*Primary Examiner*—John D. Yasko
*Assistant Examiner*—Adam J. Cermak

[57] ABSTRACT

A self-arrest overpenetration-proof cannula device for the safe insertion of a cannula or a needle with or without a catheter concentric to it into any body cavity or anatomical hollow structure having a wall, said body cavity or hollow structure being either naturally present or pathologically formed, being fluid, air or gas filled. The device has the intrinsic ability of automatically arresting the advancement of a needle or cannula instantly upon occurred body cavity penetration by the tip of said needle or cannula. The device is capable of recognizing penetration of a body cavity by means of a dropping of a vacuum pressure present in the device prior to body cavity penetration, said dropping of vacuum pressure occurring upon body cavity penetration of the needle tip, and is able to automatically respond to said drop of vacuum pressure by arresting the advancement of the needle or cannula.

12 Claims, 9 Drawing Sheets

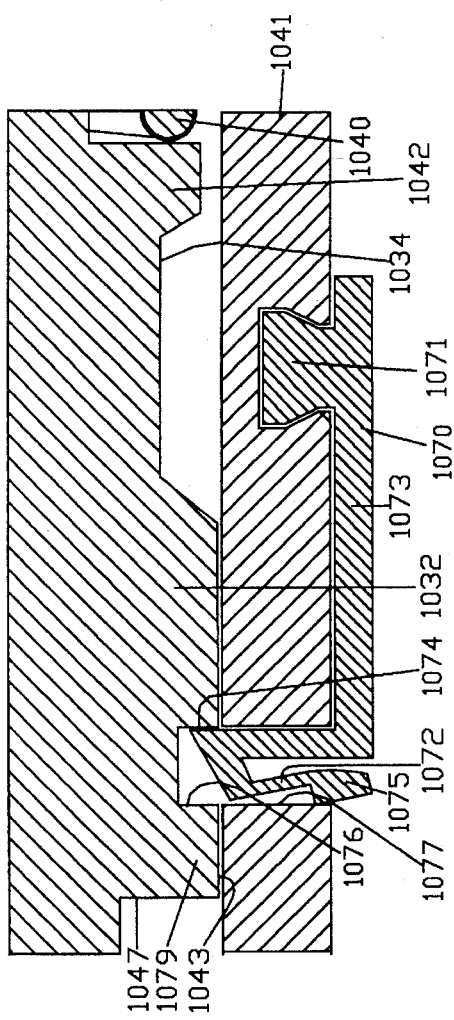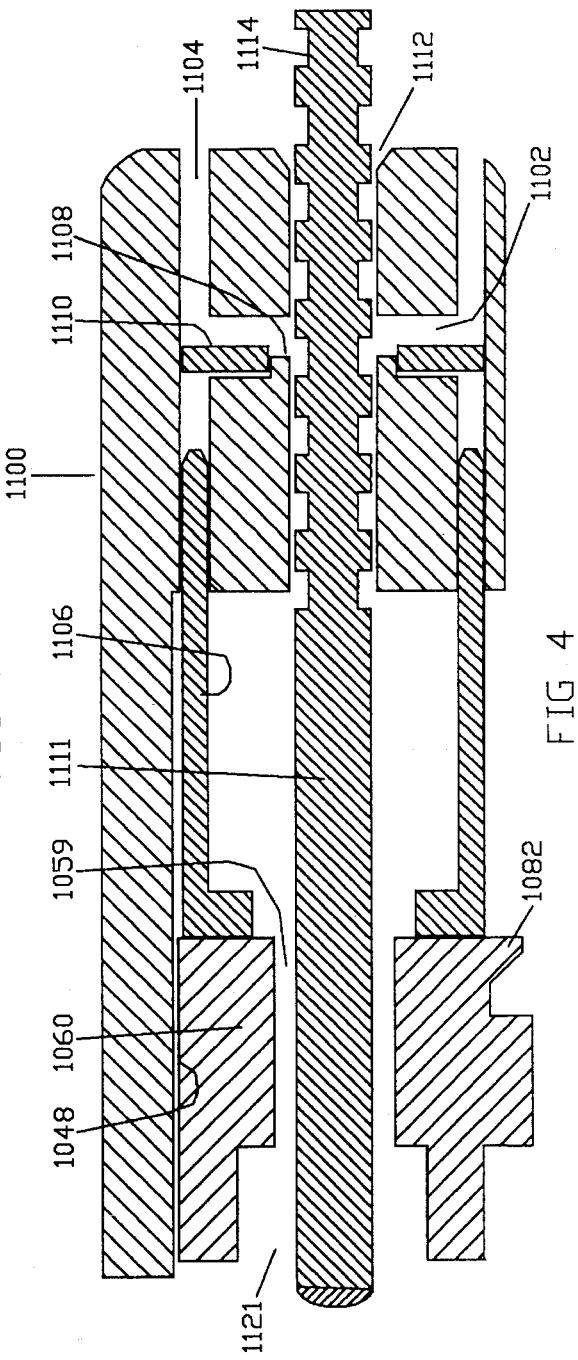

SELF-ARRESTING OVERPENETRATION-PROOF CANNULA DEVICE FOR BODY CAVITIES

BACKGROUND—FIELD OF THE INVENTION

This invention relates to medical devices apt to access body cavities more specifically to medical- surgical devices, such as surgical cannulas or needles or catheters-needles assemblies apt to access percutaneously body cavities of patients for therapeutic or diagnostic indications.

BACKGROUND—FIELD OF THE INVENTION

Placing a surgical cannula or needle with or without a catheter into a body cavity of a patient for either diagnostic or therapeutic purposes, by accessing said body cavity via the percutaneous route is a fairly common medical-surgical procedure. We list the most common procedures:

Needle-cricothyroidotony, Abdominal paracentesis, Diagnostic Peritoneal Lavage, Pleurocentesis or Thoracentesis, Pericardiocentesis, Arthrocentesis, Needle thoracostomy and Closed thoracostomy, Lumbar puncture, Subdural Aspiration in infants, Abscess aspiration, Amniocentesis, Culdocentesis, Suprapubic Bladder catheterization and Aspiration, Fluid-filled Cyst Aspiration, Hematoma evacuation, Blood drawing ,etc.

In all the above mentioned procedures a hollow needle or surgical cannula is placed by the operator within the desired anatomical space, i.e. a body cavity, naturally present or pathologically formed, either gas or air or fluid filled, for diagnostic or therapeutic purposes. In some of the above procedures a catheter usually flexible concentric to the surgical cannula or the hollow needle can be placed into the body cavity, after the body cavity has been penetrated by the cannula or needle, and sometimes such catheter may even be left in place, for instance for evacuation and drainage of the fluid contained within the body cavity.

Placing a surgical cannula or needle into a body cavity carries definite risks for the patient. Risks and complications are mainly due to overpenetration by the cannula or needle. Overpenetration can cause damage to the healthy surrounding tissues and organs. The severity of the iatrogenic injuries caused by an overpenetrating surgical cannula or needle is largely dependent upon the anatomical location of the body cavity to be accessed. The more vital and delicate are the anatomical structures in proximity of the body cavity to be accessed, the higher the risks of the procedure.

For instance the procedure of Pericardiocentesis or Needle Aspiration of fluid from the pericardium for either diagnostic or therapeutic reasons carries obvious definite risks for the patient. "Placing a needle or catheter into the pericardial space should be performed only by a skilled and experienced physician." Textbook of Advanced Cardiac Life Support, American Heart Association, second edition, page 199. Overpenetration means almost certain severe injury to the myocardium, possible laceration of coronary arteries, and possible death of the patient. It is of paramount importance that the operator recognizes pericardial space penetration by the advancing needle at the earliest stage of said penetration in order to arrest immediately the advancement of the needle. Same considerations can be made for many of the procedures above listed such as Needle Cricothyroidotomy in which a cannula with or without a catheter is placed within the trachea, accessing it via the percutaneous route, or Amniocentesis in which a needle is placed within the amniotic sac for aspiration of amniotic fluid.

The most critical factor for the operator for the successful completion of all the procedures of placement of a surgical cannula or needle with or without catheter into a body cavity is the immediate arrest of the needle advancement upon ascertainment of body cavity penetration by the tip of the needle. When a catheter-needle assembly is being used, catheter advancement into the body cavity is carded out by sliding the catheter over the needle only after ascertainment of penetration of the body cavity by the tip of the needle.

In order to facilitate ascertainment of the occurred penetration of the body cavity by the needle tip, the operator preferably connects a syringe to the needle or cannula and by withdrawing the plunger of the syringe after the tip of the needle or cannula has been inserted into the skin or tissues overlaying the body cavity, he, or she, aspirates constantly during the advancement and passage of the cannula or needle through the tissues or walls overlying the body cavity, creating a negative pressure, within the syringe ahead of the plunger, which results in a resistance to withdrawal of the plunger. When the tip of the needle, passing through the tissues overlying the body cavity, enters the body cavity, air or fluid is aspirated into the syringe connected to the needle or cannula and, as a result of that, the negative pressure in front of the plunger suddenly drops and, consequently, the resistance to withdrawal of the plunger being held by the operator suddenly falls. The fall of resistance to withdrawal of the plunger alerts the operator of the occurred body cavity penetration. At this point the operator promptly arrests the advancement of the needle or cannula in order to avoid overpenetration and damage to the surrounding tissues with possible dreadful consequences, local and systemic, for the patient.

From the above description of the procedure, it is apparent that the following procedural steps are critical for the operator:
1) To ascertain body cavity penetration at the earliest stage of penetration by the needle tip of the cannula or needle, and
2) To arrest the needle advancement immediately, as soon as body cavity penetration is ascertained.

A search in the Patent Office has revealed no surgical cannula or needle capable of sensing body cavity penetration and self arrest of the advancing needle in response to body cavity penetration based on the principle outlined below.

BRIEF SUMMARY OF THE INVENTION

The disadvantages of the present apparatus and methods of cannula or needle placement into a body cavity are overcome with the present invention.

With the present application we propose a Self-arresting Overpenetration Proof Cannula Device. Our device is able to place a surgical cannula or needle into a body cavity without the risk inherent to the devices and methods presently used.

The principle our device is based upon is the intrinsic ability of the device to automatically respond with a self-arresting mechanism stopping the advancement of the needle or cannula instantly upon occurred body cavity penetration by the tip of the needle or cannula. The device is capable of recognizing penetration of a body cavity by means of a dropping of a vacuum pressure present in the device prior to body cavity penetration, said dropping of vacuum pressure occurring upon body cavity penetration of the needle tip, and is able to automatically respond to said drop of vacuum pressure by arresting the advancement of the needle or cannula. No known device is capable to do so based in the above outlined principle.

With our device, the operator, after arming the device by creating a vacuum pressure at the proximal end of the needle or cannula, advances the needle or cannula through the tissues overlying the body cavity. The device, as outlined above, instantly recognizes body cavity penetration by the needle tip and it is capable of instantly and automatically arresting any further advancement of the needle or cannula avoiding any risks of overpenetration.

Subsequent optional advancement of a catheter over the cannula or needle at the earliest time of said penetration is achieved either automatically in a preferred embodiment, or manually.

Risks and complications due to overpenetration of the advancing needle with our device are practically non existing.

The advantages of the present invention are preferably attained by a self arresting overpenetration proof cannula device comprising a cannula or needle, with or without a catheter concentric with said cannula or needle, means sensing body cavity penetration by said cannula or needle and means arresting the advancement of said cannula or needle automatically upon penetration of the body cavity by said penetrating needle.

When a catheter-needle assembly is used, the device is also provided with manual or resilient means urging said catheter to an advanced position and means for triggering the resilient means of catheter advancement into a body cavity upon body cavity penetration. The triggering means releasing catheter advancement may be manual or may be fully automatized in response to body cavity penetration of the needle tip.

Another object of the present invention is to provide an improved Self-arresting Cannula Device which permits one handed insertion and placement of a cannula, needle or catheter within any body cavity without risk for the patient.

Another object of the present invention is to provide the operator with a safe Self-arresting Cannula Device which includes means of controlled penetration and arrest of the cannula or needle advancement into any body cavity entirely obviating to reliance upon potentially failing human factors which could lead to overpenetration and damage to the tissues and organs surrounding body cavities.

BRIEF DESCRIPTION OF THE DRAWINGS

FIG. 3 is a cross section view of a detail of the device, specifically of the trigger of the device prior to use.

FIG. 4 is a cross section of a detail of device, specifically of the arrest unit, prior to use.

DETAILED DESCRIPTION OF THE DEVICE

Figure 1:
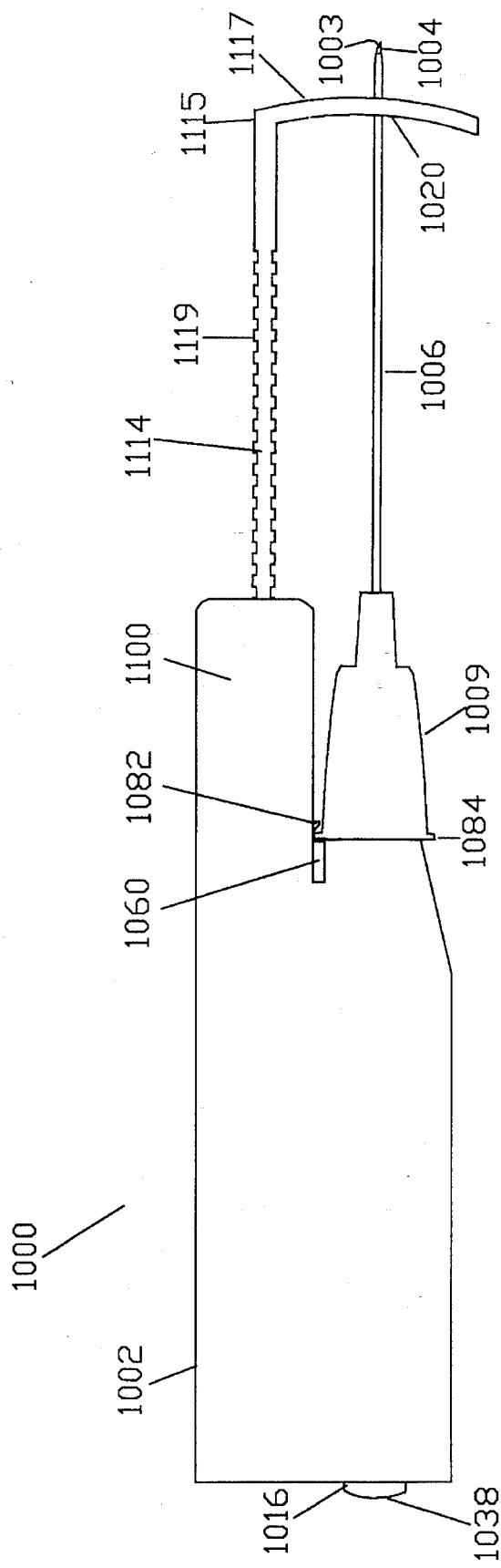
FIG. 1 is a side view of the device in position of rest prior to use.

FIG. 1 is a side view of the device, generally indicated at 1000 in a stage prior to use. The device is composed of three main parts: a housing 1002, a cannula or needle 1004, and a catheter 1006.

Figure 2:
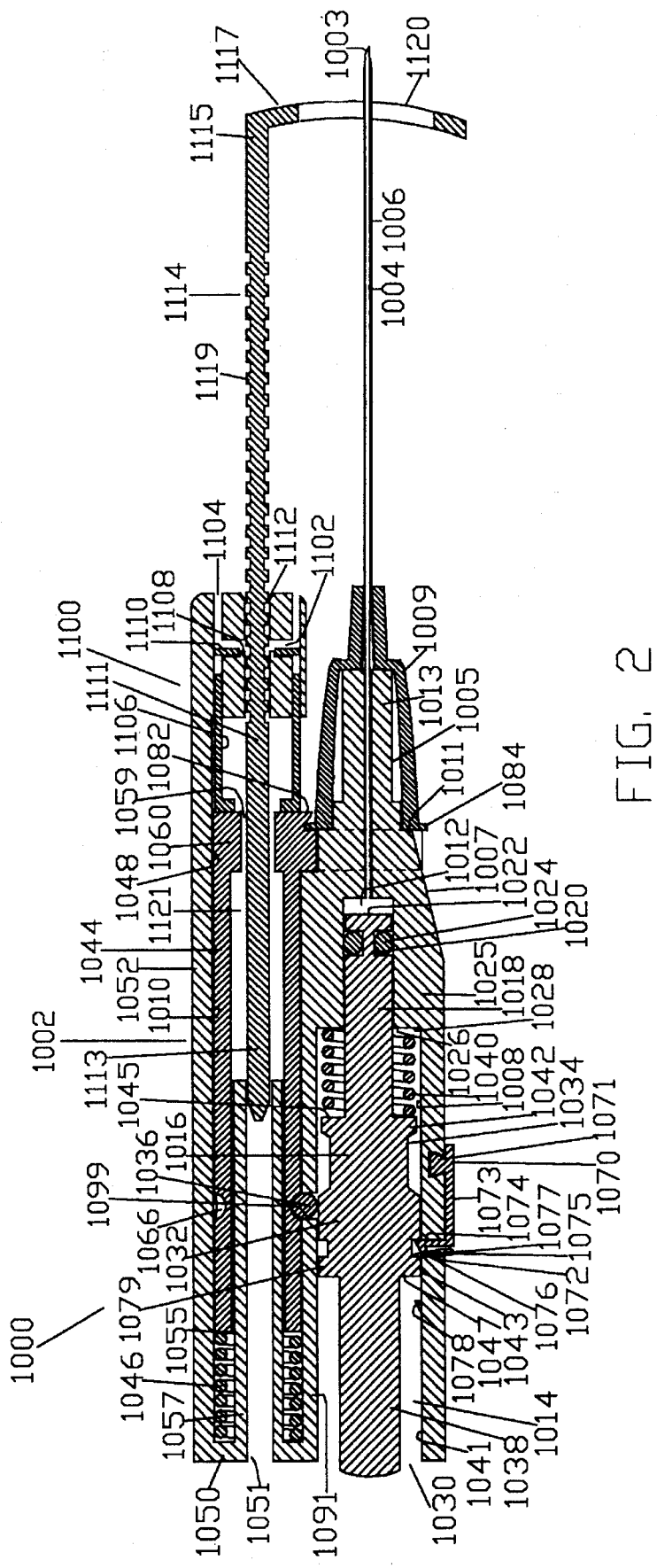
FIG. 2 is a cross section of the device of FIG. 1 in position of rest prior to use.

As best seen in FIG. 2, which is a cross section of the device prior to use, housing 1002 is composed of two parallel chambers of generally cylindrical shape, piston chamber 1008, interface member chamber 1010 and of an arresting unit or means 1100.

Needle hub 1005 connected to housing 1002, protrudes from anterior lower end 1007 of housing 1002. Needle hub 1005 has base 1011 which precisely fits within catheter hub 1009 of catheter 1006 and has nozzle 1013 in continuity with needle hub base 1011 to allow adequate leeway for release of catheter hub 1009 of catheter 1006 from hook 1082 of front end 1060 of intermediate member 1044, when catheter 1006 is advanced as it will be described in the description of the operation.

Piston chamber 1008, delimited laterally by sidewall 1041, is composed of an anterior or vacuum chamber 1012 in communication with hollow needle 1004, and a posterior chamber 1014 of larger diameter than vacuum chamber 1012. Posterior chamber 1014 is in continuity of vacuum chamber 1012 via opening 1026, with collar 1028 encircling opening 1026. Posterior chamber 1014 is open posteriorly via opening 1030. In piston chamber 1008 is slideably mounted piston 1016. Piston 1016 is composed of three segments: anterior segment 1018, intermediate segment 1032 and posterior segment 1038. Anterior segment 1018 is partially contained in vacuum chamber 1012 and partially in posterior chamber 1014. The anterior segment 1018 of piston 1016 has an annular groove 1020 formed in proximity of its front end 1022, where O-ring 1024 is mounted in airtight fashion with wall 1025 of vacuum chamber 1012. Spring 1040 is mounted around anterior piston segment 1018, between collar 1028 and flange 1042 of intermediate piston segment 1032. The intermediate segment 1032 of piston 1016, in continuity with anterior piston segment 1018, is of larger diameter than anterior piston segment 1018 in order to fit in chamber 1014 of larger diameter. Intermediate piston segment 1032 has front face 1045, posterior face 1047 and side face 1043. As better seen in FIG. 3, intermediate piston segment 1032 from back to front is formed with posterior flange 1079, annular recess 1076 for trigger member 1070, wide annular recess 1034 for ball member 1036 and anterior flange 1042. Posterior piston segment 1038, in continuity with intermediate piston segment 1032, extends posteriorly through opening 1030 of chamber 1008.

Trigger member or means 1070 is mounted in side wall 1041 of piston chamber 1008, inferiorly. As better seen in FIG. 3, trigger member 1070 is composed of stub 1073 fastened to wall 1041 via fastener 1071 and resilient latch 1072, grossly U shaped, mounted within window 1077 of side wall 1041 of piston chamber 1008. Latch 1072 has arrest tooth 1074 engaged within annular recess 1076 of intermediate piston member 1038, releasably locking piston 1016 and latch locking tooth 1075.

Within posterior chamber 1014, posterior to intermediate segment piston 1032 and protruding inferiorly from side wall 104 1, is arrest pin 1078.

Interface member chamber 1010 of general cylindrical shape is delimited laterally by side wall 1052, open anteriorly via opening 1048 and open posteriorly via centrally located opening 105 1, within posterior wall 1050. Spring 1046 is also contained in interface member chamber 1010, posteriorly to interface member 1044, seating on posterior wall 1050, being interposed between side wall 1052 and inner wall 1057 of interface member chamber 1010.

Interface or intermediate member 1044 of general cylindrical hollow shape, slideably mounted within intermediate member chamber 1010, has at front end 1060 formed with passageway 1059 for arrest rod 1102. The posterior segment of intermediate member 1044 being positioned, with the device in position of rest, between side wall 1052 and inner walls 1057 of interface member chamber 1010. Front end 1060 of intermediate member 1044 engages catheter hub 1009 by hook 1082 releasably engaging catheter hub flange 1084. Interface member 1044 is also formed with annular recess 1066 for ball member 1036 as it will be explained below.

Arrest unit 1100 of general cylindrical shape is at the front and superior end of housing 1002. Arrest unit 1100 is isoaxial and distal to interface member chamber 1010 being in continuity with it by side wall 1052 prolonging forward up to connect with arrest unit 1110 as best seen in FIG. 1.

As best seen in FIG. 4, arrest unit 1100 is formed with cylindrical seating 1104 where push-cylinder 1106 is slideably mounted, annular recess 1102 where centripetal resilient arrest ring 1110 is mounted and central axial passageway 1112 for arrest rod 1114. Push-cylinder 1106 is with the device in position of rest, resting on front end 1060 of interface member 1044. Push-cylinder 1106 can however also be constructed as integral part of interface member 1044 in continuity with front end 1060 of interface member 1044. Centripetal resilient arrest ring 1110 is not allowed to tightens on arrest rod 1114 by circular arrest 1108. As best seen in FIG. 2, arrest rod 1114 is composed of shaft 1111, proximal end 11. 13 and distal end 1115 to which arrest plate 1117 is firmly attached at angle. Arrest rod 1114 in position of rest is slideably concentrically mounted from back to front within hollow space or cavity 1121 of interface member 1044, passageway 1059 of front end 1060 of intermediate member 1044 and passageway 1112 of arrest unit 1110. Rod 1114 presents multiple indentations 1119 for arrest ring 1110. Arrest plate 1117 has opening 1120 large enough to permit the passage of needle 1004, catheter 1006 and catheter hub 1009 as it will be explained in the description of the operation.

Interface member chamber 1010 and piston chamber 1008 are separated for the whole length by devider wall 1091. A window 1099 is formed in the devider wall 1091 to house ball member 1036. As shown in FIG. 2 with the device in position of rest, prior to use ball member 1036 is shown engaged in window 1099 of divider wall 1091, seating inferiorly on side wall of piston 1016 and, superiorly, locking intermediate member 1044 by engaging correspondent annular recess 1066 of interface member 1044.

Hollow needle 1004 has a tip 1003 and protrudes from needle hub 1005 which has been previously described.

Catheter 1006 with hub 1009 is slideably mounted respectively over needle 1004 and needle hub 1005.

DESCRIPTION OF THE OPERATION

Figure 5:
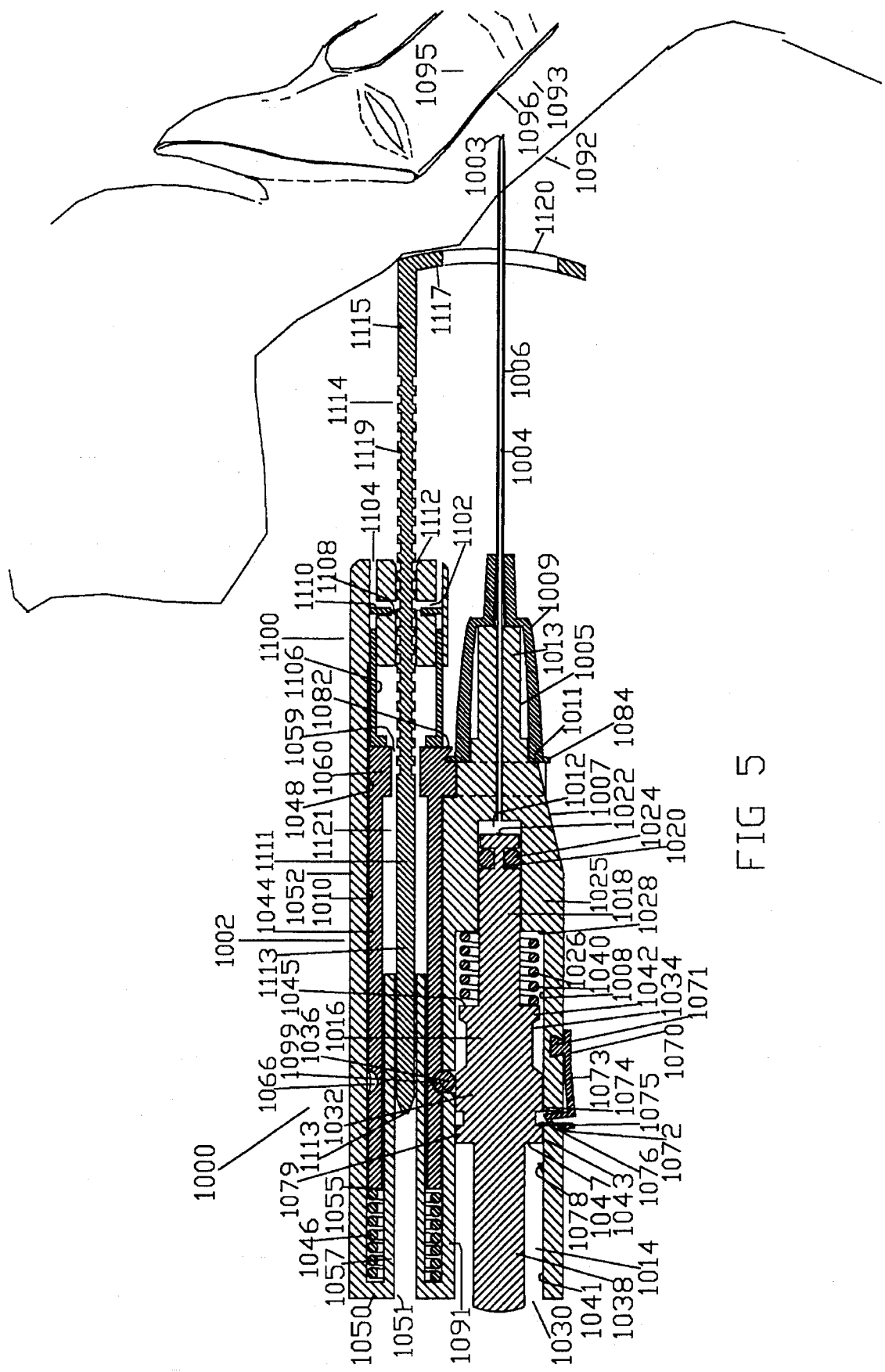
FIG. 5 is a cross section of the device of FIG. 1 shown in armed position, after penetration of the overlying tissue of the body cavity, in this case the trachea, but prior to body cavity penetration.

FIGS. 5 to 8 show the device in use. The body cavity represented in this case is the trachea for description purpose only. The device can be used for any body cavity or anatomical hollow structure having walls of the human body naturally present or pathologically formed, either air or gas or fluid filled. As seen in FIG. 5, in use, the operator, pushes forward piston 1016 by acting upon posterior piston segment 1038. Trigger latch 1072 will be displaced outwardly by posterior flange 1079 of intermediate piston segment 1038 unlocking so piston 1016. Locking latch- tooth 1075 will unreleasably lock latch 1075 outwardly. With piston 1016 maintained in a fully advanced position by the operator hand acting upon posterior piston segment 1038, the operator penetrates skin 1092 of pretracheal space or body cavity wall 1093 with needle tip 1003. Grip on posterior piston segment or plunger 1038 is then released by the operator when needle tip 1003 is well under skin 1092. Posterior displacement of piston 1016 urged posteriorly by spring 1040 will create a vacuum in front of piston head 1022. However due to the sealing qualifies of the skin and subcutaneous tissue of pretracheal tracheal space 1093, piston 1016 will be posteriorly displaced by only a fraction as shown in FIG. 5. Needle 1004 with its catheter 1006 concentric to it, is then advanced by the operator through the pretracheal space 1093. Arrest rod 1114 will be displaced posteriorly during this maneuver as arrest plate 1117 will be impeded to advance by coming in contact with the neck of the patient.

Figure 6:
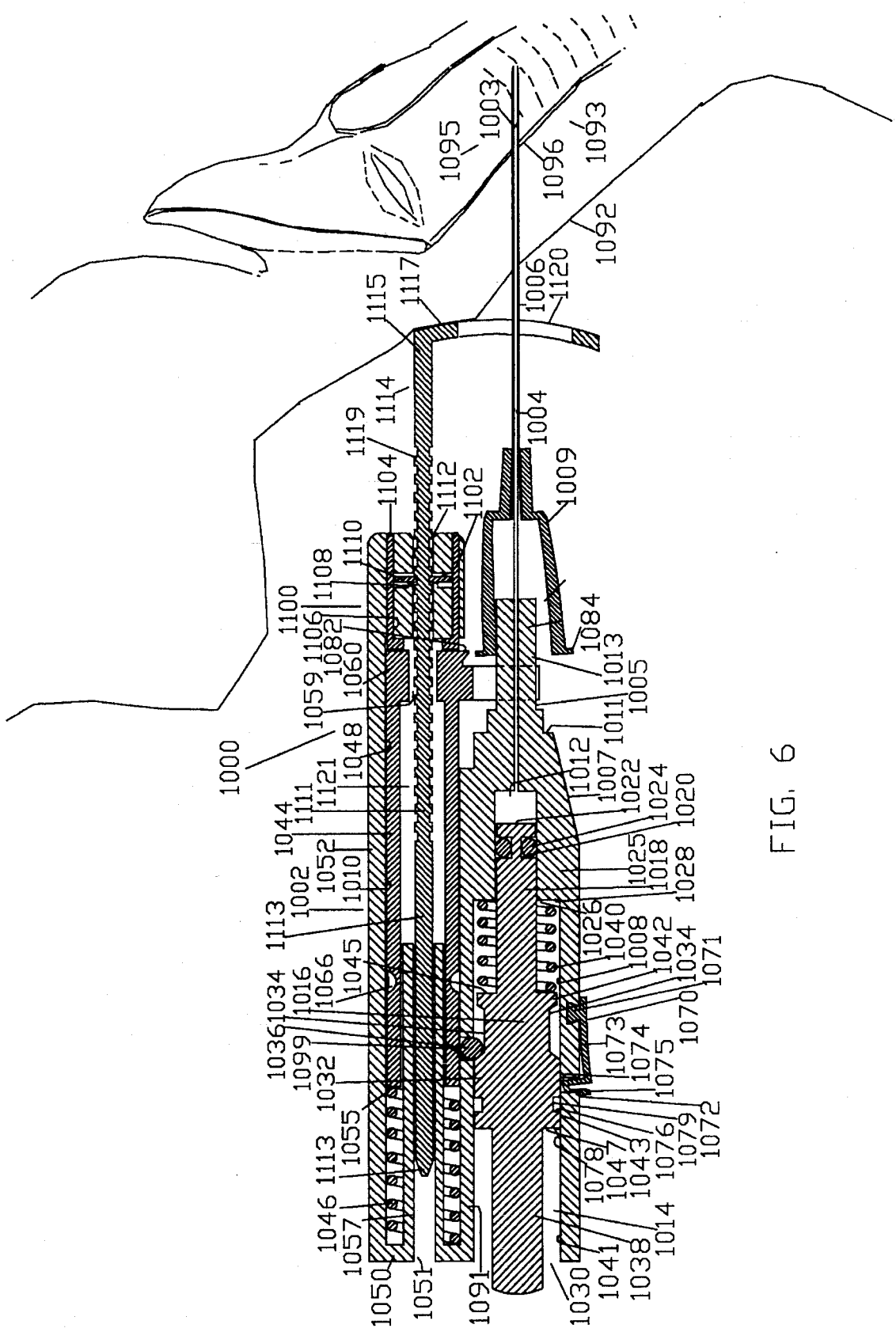
FIG. 6 is a cross section view of the device after penetration of the body cavity by the needle tip. Advancement of a catheter into the body cavity is shown along with the actuation of the arrest unit resulting in locking of the arrest rod.

As best seen in FIG. 6, as soon as needle tip 1003 will penetrate tracheal space or body cavity 1095 by penetrating through cricothyroid membrane 1096, backflow of the content of body cavity 1095, air, gas or fluid, is accelerated through hollow needle 1004 into vacuum chamber 1012 by the presence of the vacuum. Vacuum pressure in front of piston 1018 will vanish or will be reduced allowing so posterior displacement of piston 1016 up to arrest tooth 1078. As seen in FIG. 5, ball 1036, forwardly -urged by spring or resilient means 1046 via annular recess 1066, due to its eccentric position with its equator below the upper edge of window 1099, no longer retained in window 1099 of devider wall 091 will fall in wide annular recess 1034 of piston 1016 releasing so interface member 1044 from it locked starting position, free so to be urged forward by the action of spring 1046. Interface member 1044 advancement by spring or resilient means 1046 will lock arrest rod 1114 and cause also advancement of catheter 1005 by interface member front end 1060 acting upon flange 1084 of catheter hub 1009.

Figure 7:
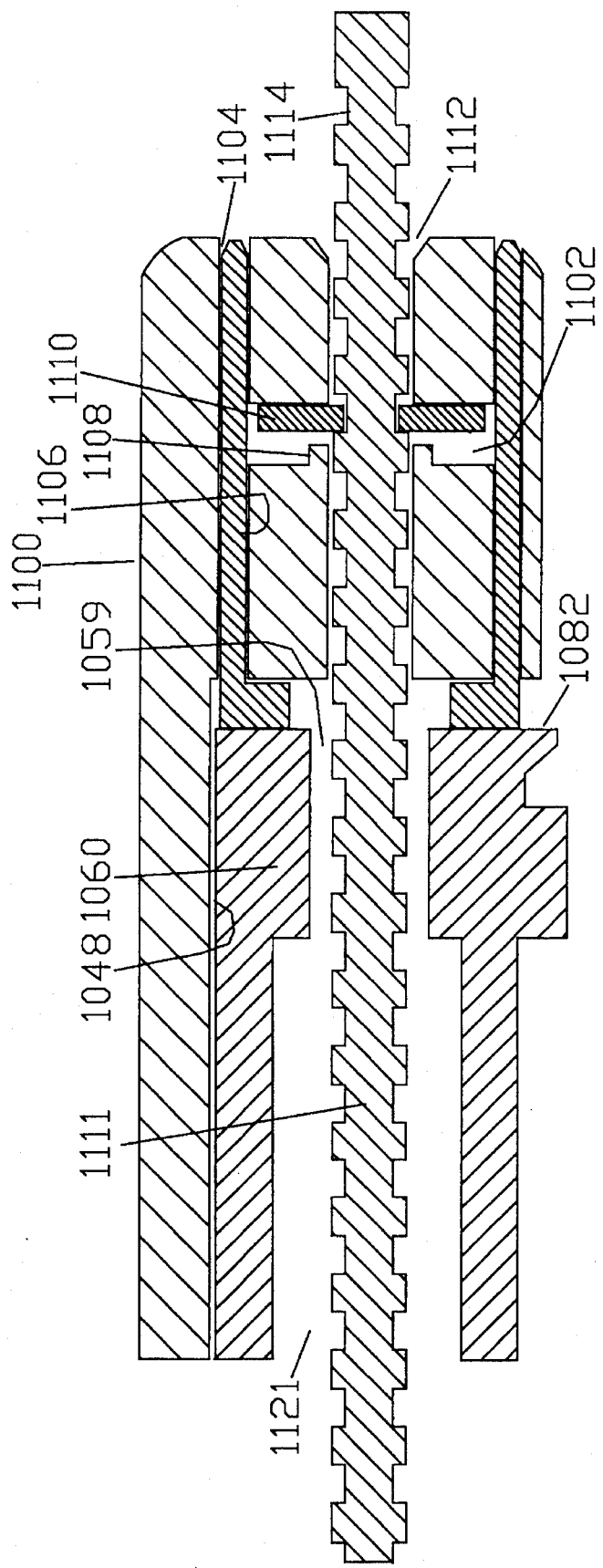
FIG. 7 is a cross section view of a detail of the device specifically of the arrest unit shown in FIG. 4, actuated.
Figure 8:
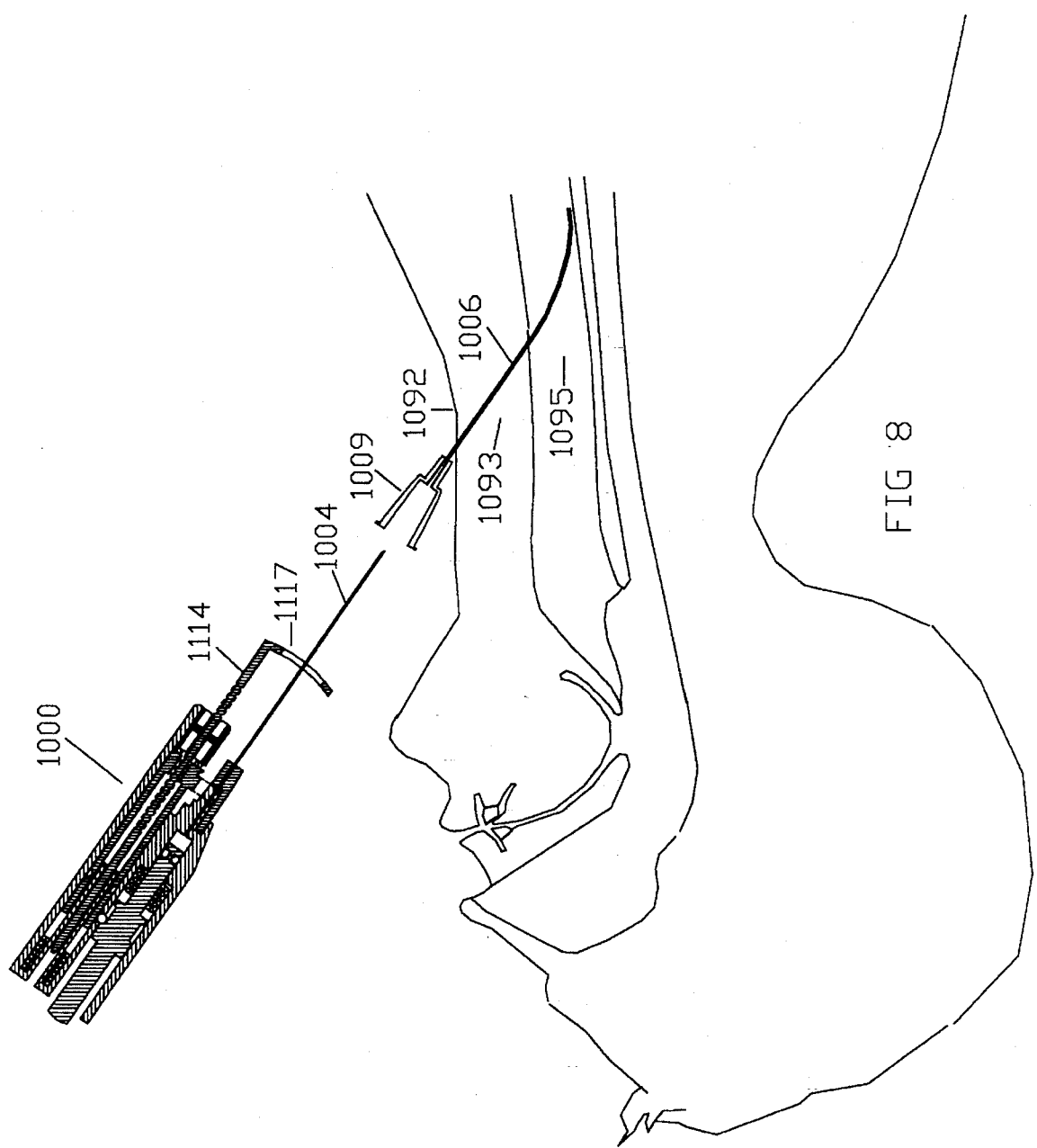
FIG. 8 is a cross section view of the device of FIG. 1 as used, in relation to the patient anatomy with the catheter in place within the body cavity ready to be used for therapeutic or diagnostic reasons.

As seen in FIG. 6 and 7, advancement of front end 1060 of interface member 1044 will displace forward push-cylinder 1116 which in turn will displace forward arrest ring 1110, dislodging it from its resting position i.e. seating on arrest tooth 1118. Arrest ring 1110 no longer retained in the expanded position by arrest tooth 1118 will be able to tightens around the nearest of the indentations 1119 of arrest rod 1114 causing so its locking. Needle 1004 will be no longer advanceable into the tracheal space due to plate 1117 resting in locked position over skin 1092 of the pretracheal space 1093. Advancement of catheter 1006 will be carried out by front end 1060 of intermediate member 1044 for the whole length of needle base 1011. Front end 1060 will then loose engagement with catheter hub 1009 due to the fact that catheter hub 1009 will rest on needle nozzle 1013 of smaller diameter. Further advancement of catheter 1006 can be accomplished manually of as best seen in FIG. 9 by the operator until optimal positioning is reached within the tracheal lumen or body cavity 1095.

Figure 9:
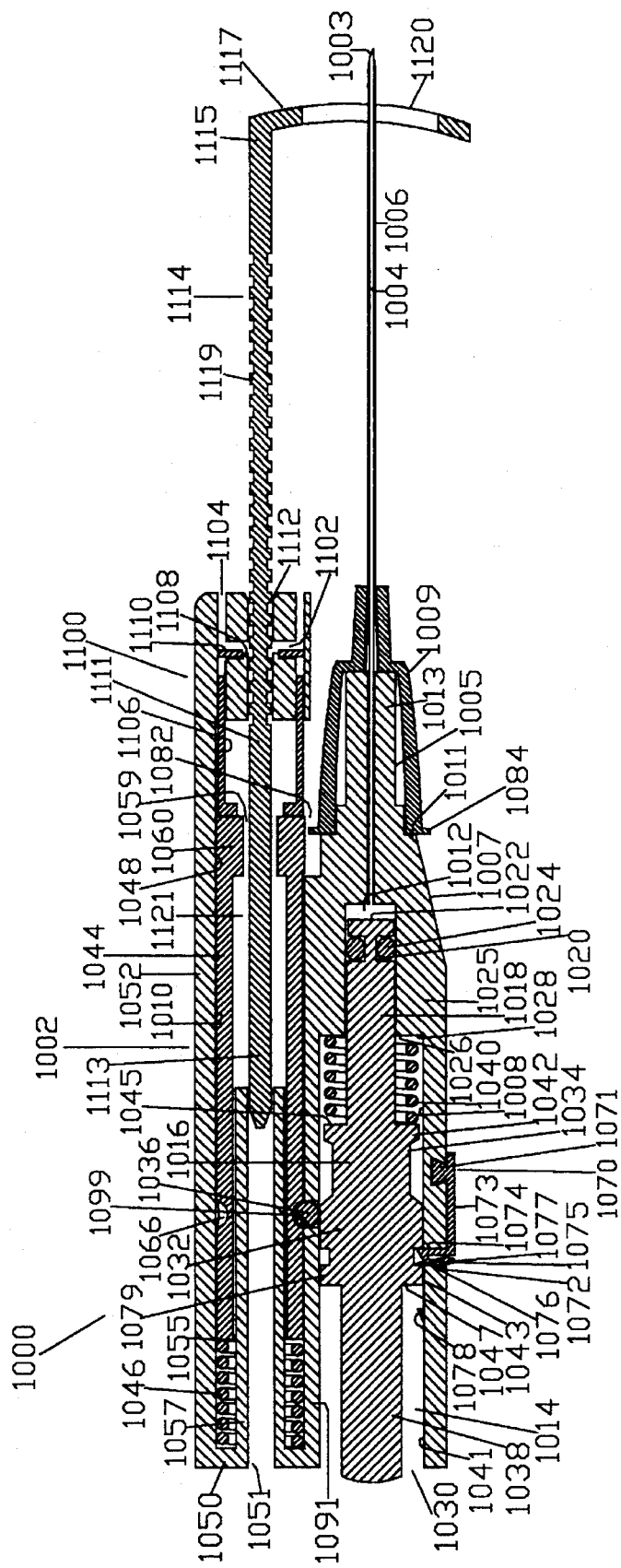
FIG. 9 is a cross section view of an alternative form of the device prior to use in which the catheter is advanceable manually.

FIG. 9 shows an all similar version of the device described in FIGS. 1 to 8 except that the catheter is advanced manually by the operator. The only structural difference is that the front end 1060' of interface 1044 is not engaging catheter hub 1009. The device is operated exactly as the previously described device, however advancement of interface member 1044 will only cause arrest of arrest rod 1114. Catheter 1006 will have to be advanced by hands by the operator grabbing it by the hub 1009.

Figure 10:
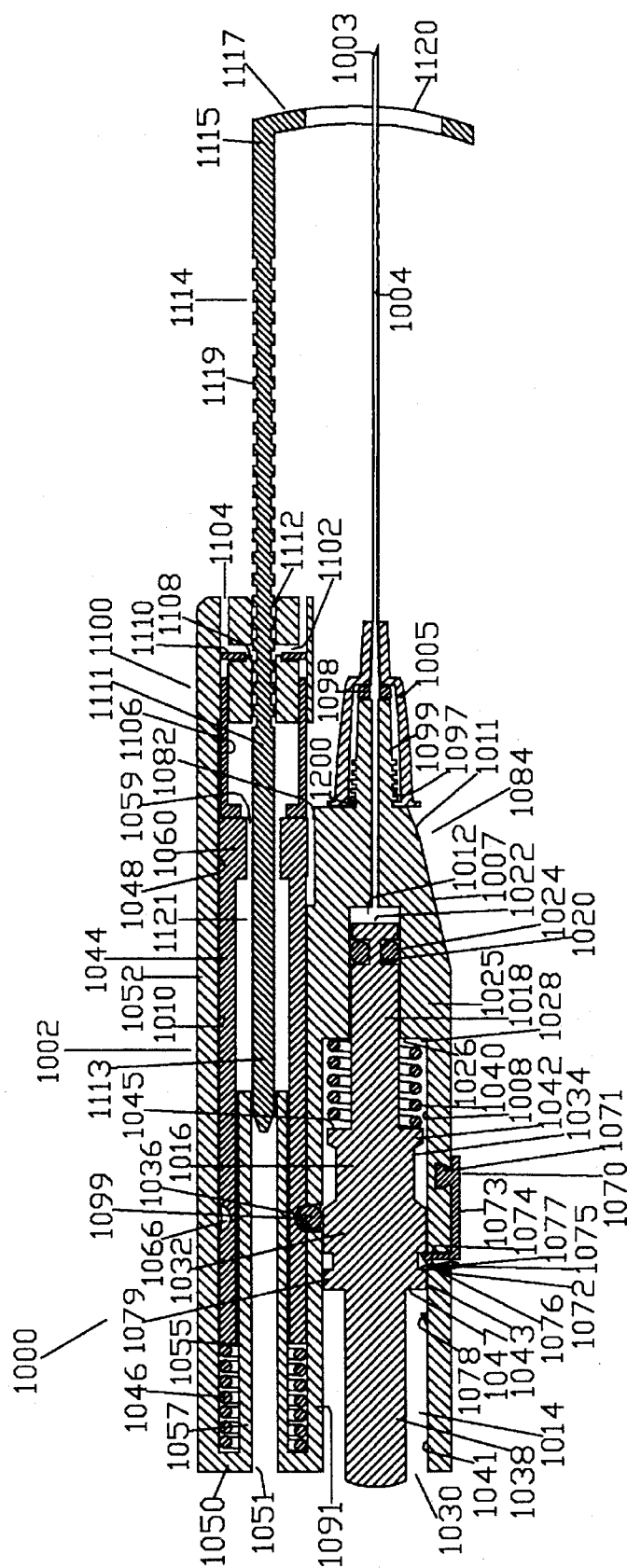
FIG. 10 shows an alternative form of the device prior to use in which the cannula or needle is detacheable from the device.

FIG. 10 shows an all similar version of the device described in FIGS. 1 to 8 except that in this version there is no catheter concentric to the needle or cannula and the cannula or needle is detacheable from the device. In this version of the device, cannula or needle 1004 is connected with its hub 1005 in a detacheable air tight fashion to housing 1002 via flange 1200 of hub 1005 screwed on thread 1097 of nozzle 1099 of housing 1002. The presence of sealing ring 1098 further insures the air tightness. The device is operated as the previously described device without a catheter. In this case once a body cavity is penetrated by the needle tip 1003 and arresting means or unit 1100 is actuate& the operator can detach needle 1004 from housing 1002 by unscrewing needle 1004 from housing 1002, leaving needle 1004 front portion within the body cavity for whatever use, such as fluid aspiration or drainage. Needle hub 1005, if necessary, will be ready for any connection.

What we claim is:

1. A body cavity access device for insertion of a cannula into a body cavity, comprising:

a cannula, vacuum means to house a vacuum pressure, said vacuum means being in communication with said cannula, means for arresting an advancement of said cannula through body tissues overlying said body cavity, said arresting means being automatically actuable in response to a change of said vacuum pressure occurring upon penetration of said body cavity by said cannula.

2. The device of claim 1 wherein said change of a vacuum pressure within said vacuum means includes a reduction of said vacuum pressure within said vacuum means.

3. The device of claim 1 wherein said change of a vacuum pressure within said vacuum means includes a vanishing of said vacuum pressure within said vacuum means.

4. The device of claim 1, further comprising:

a catheter concentric to said cannula, said catheter being manually advanceable into said body cavity upon penetration of said body cavity by said cannula.

5. The device of claim 1, further comprising:

a catheter concentric to said cannula, said catheter being automatically advanceable into said body cavity upon penetration of said body cavity by said cannula.

6. A body cavity access device for placement of a cannula into a body cavity, comprising:

a cannula, means for accelerating backflow of content of said body cavity, said accelerating means being in flow communication with said cannula, said backflow occurring upon penetration of said body cavity by said cannula, means for arresting an advancement of said cannula through body tissues overlying said body cavity, said arresting means being automatically actuable in response to said accelerated backflow of content of said body cavity.

7. A body cavity access device for insertion of a catheter into a body cavity, comprising:

a catheter, a hollow needle having a tip, said catheter being concentric with said hollow needle, said hollow needle being advanceable toward a body cavity, vacuum means to house a vacuum pressure, said vacuum means being in communication with said hollow needle, means for arresting an advancement of said needle through body tissues overlaying said body cavity, said arresting means being automatically actuable in response to a change of said vacuum pressure occurring upon penetration of said body cavity by said needle tip, said catheter being advanceable into said body cavity upon needle tip penetration of said body cavity.

8. The device of claim 7 wherein said catheter is automatically advanced to an advanced position relative to said needle upon body cavity penetration of said needle.

9. The device of claim 8 wherein said catheter is manually advanced to an advanced position relative to said needle upon body cavity penetration of said needle.

10. A body cavity access device for placement of a catheter into a body cavity comprising:

a catheter, a hollow needle having a tip, said catheter being concentric with said hollow needle, said needle being advanceable toward a body cavity, means for accelerating backflow of content of said body cavity, said accelerating means being in flow communication with said hollow needle, said backflow occurring upon penetration of said body cavity by said needle tip, means for arresting an advancement of said needle through body tissues overlaying said body cavity, said arresting means being automatically actuable in response to said accelerated backflow of content of said body cavity, said catheter being advanceable into said body cavity upon needle tip penetration of said body cavity.

11. A body cavity access device for placement of a catheter into a body cavity, comprising:

a catheter, a hollow needle having a tip, said catheter being concentric with said hollow needle, said needle being advanceable toward a body cavity, means for arresting an advancement of said needle through body tissues overlaying a body cavity, said arresting means being automatically actuated upon penetration of said body cavity by said needle tip, said catheter being advanceable into said body cavity upon needle tip penetration of said body cavity.

12. A body cavity access device for placement of a catheter into a body cavity, comprising:

a catheter, a hollow needle having a tip, said catheter being concentric with said needle, said needle being advanceable toward a body cavity, means for preventing overpenetration of said body cavity by said hollow needle, said means for preventing overpenetration being automatically actuated upon penetration of said body cavity by said needle tip, said catheter being advanceable into said body cavity upon needle tip penetration of said body cavity.

* * * * *